United States Patent
Orban (10) Patent No.: US 11,286,303 B2
(45) Date of Patent: *Mar. 29, 2022

(54) CTLA4 FUSION PROTEINS FOR THE TREATMENT OF DIABETES

(71) Applicant: Phaim Pharma Ltd, London (GB)

(72) Inventor: Tihamer Orban, London (GB)

(73) Assignee: Phaim Pharma Ltd, London (GB)

( * ) Notice: Subject to any disclaimer, the term of this patent is extended or adjusted under 35 U.S.C. 154(b) by 281 days.

This patent is subject to a terminal disclaimer.

(21) Appl. No.: 16/356,445

(22) Filed: Mar. 18, 2019

(65) Prior Publication Data

US 2019/0211105 A1   Jul. 11, 2019

Related U.S. Application Data (63) Continuation of application No. 14/576,990, filed on Dec. 19, 2014, now Pat. No. 10,233,242, which is a continuation of application No. 14/021,629, filed on Sep. 9, 2013, now abandoned, which is a continuation of application No. 13/534,560, filed on Jun. 27, 2012, now abandoned.

(51) Int. Cl.
| | |
|---|---|
| *A61K 38/17* | (2006.01) |
| *C07K 14/705* | (2006.01) |
| *A61K 39/395* | (2006.01) |
| *A61K 9/107* | (2006.01) |
| *A61P 3/10* | (2006.01) |
| *C07K 16/28* | (2006.01) |
| *A61K 9/00* | (2006.01) |
| *A61K 39/00* | (2006.01) |

(52) U.S. Cl.
CPC ...... *C07K 16/2827* (2013.01); *A61K 38/1774* (2013.01); *C07K 14/70521* (2013.01); *C07K 16/2818* (2013.01); *A61K 9/0019* (2013.01); *A61K 2039/505* (2013.01); *C07K 2317/76* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | |
|---|---|---|
| 5,434,131 A | 7/1995 | Linsley et al. |
| 5,814,321 A | 9/1998 | Miyahara et al. |
| 5,844,095 A | 12/1998 | Linsley et al. |
| 5,851,795 A | 12/1998 | Linsley et al. |
| 5,976,538 A | 11/1999 | Hilgers et al. |
| 6,110,746 A | 8/2000 | Cohen et al. |
| 6,235,282 B1 | 5/2001 | Riviere et al. |
| 6,299,884 B1 | 10/2001 | Van et al. |
| 6,797,269 B2 | 9/2004 | Mosca et al. |
| 7,041,634 B2 | 5/2006 | Weber et al. |
| 7,304,033 B2 | 12/2007 | Larsen et al. |
| 7,455,835 B2 | 11/2008 | Cohen et al. |
| 8,497,247 B2 | 7/2013 | Cohen et al. |
| 8,652,488 B2 | 2/2014 | Orban |
| 8,735,359 B2 | 5/2014 | Orban |
| 10,233,242 B2* | 3/2019 | Orban ............... C07K 16/2818 |
| 2002/0114814 A1 | 8/2002 | Gray et al. |
| 2003/0022836 A1 | 1/2003 | Larsen et al. |
| 2003/0045467 A1 | 3/2003 | Orban |
| 2003/0190323 A1 | 10/2003 | Cohen et al. |
| 2004/0136998 A1 | 7/2004 | Bander |
| 2004/0151725 A1 | 8/2004 | Gray et al. |
| 2004/0202650 A1 | 10/2004 | Gribben et al. |
| 2006/0183670 A1 | 8/2006 | Orban |
| 2008/0019999 A1 | 1/2008 | Vratsanos et al. |
| 2008/0160022 A1 | 7/2008 | Larsen et al. |
| 2009/0016968 A1 | 1/2009 | Wang et al. |
| 2009/0142308 A1 | 6/2009 | Orban et al. |
| 2009/0246212 A1 | 10/2009 | Koshiba et al. |
| 2011/0250225 A1 | 10/2011 | Fotin-Mleczek et al. |
| 2011/0311529 A1 | 12/2011 | Cohen et al. |
| 2012/0258094 A1 | 10/2012 | Cohen et al. |
| 2013/0315904 A1 | 11/2013 | Orban |
| 2013/0316375 A1 | 11/2013 | Orban |
| 2014/0099306 A1 | 4/2014 | Orban |
| 2014/0134152 A1* | 5/2014 | Willimas ........... A61K 38/4853 424/94.64 |
| 2014/0220015 A1 | 8/2014 | Orban |
| 2015/0104451 A1 | 4/2015 | Orban |
| 2016/0299128 A1 | 10/2016 | Orban |

(Continued)

FOREIGN PATENT DOCUMENTS

| | | |
|---|---|---|
| CN | 101255192 A | 9/2008 |
| CN | 101896499 A | 11/2010 |

(Continued)

OTHER PUBLICATIONS

Scanduzzi et al. (2011) Discovery Medicine 12(63): 119-128.*
Meylan et al. (2011) Immunol Rev. 244(1): 1-13.*
Gerdes et al. (2011) Thromb Haemost. 106: 804-813.*
Ribot et al. (2011) Cell. Mol. Life Sci. 68: 2345-2355.*
Moon et al. (2011) Diabetes 60: 1647-1656.*
Leibowitz et al. (2011) J Diabetes Invest. 2: 82-91.*
Wei et al. (2011) Endocrine Journal 58(10): 819-825.*
Dayan et al. (2019) Lancet 394: 1286-1296.*
Gaglia et al. (2019) Biochemistry 58: 4107-4111.*

(Continued)

*Primary Examiner* — Ilia I Ouspenski (74) *Attorney, Agent, or Firm* — Womble Bond Dickinson (US) LLP (57) ABSTRACT

A method of treating, preventing, or delaying the progression of Type 1 diabetes mellitus autoimmunity by administering an effective amount of a cytotoxic T-lymphocyte-associated antigen 4 (CTLA4) molecule is provided herewith. The CTLA4 molecule may be a fusion protein of a CTLA4 extracellular region and an immunoglobulin, such as abatacept.

20 Claims, 4 Drawing Sheets

(56) References Cited

U.S. PATENT DOCUMENTS

2016/0361397 A1    12/2016  Orban et al.
2020/0268883 A1*    8/2020  Orban ............... A61K 39/0008

FOREIGN PATENT DOCUMENTS

| EP | 1248802 B1 | 7/2004 |
|---|---|---|
| JP | 2005-522987 | 8/2005 |
| RU | 2283847 C2 | 9/2006 |
| WO | 99/49734 A1 | 10/1999 |
| WO | 02/53106 | 7/2002 |
| WO | 03/35678 | 5/2003 |
| WO | 2007/037544 A1 | 4/2007 |
| WO | 2009/029847 A1 | 3/2009 |
| WO | 2009/120341 A2 | 10/2009 |
| WO | 2012/001647 A2 | 1/2012 |
| WO | 2012/015903 A1 | 2/2012 |

OTHER PUBLICATIONS

Marelli-Berg et al., "A two-signal model for T cell trafficking." A Trends Immunol Jun. 2007, vol. 28, No. 6, pp. 267-273.
Lo et al. "Selective targeting of human alloresponsive CD8+ effector memory T cells based on CD2 expression", Am. J. Transplant., vol. 11, 2011, pp. 22-33.
Liping et al., "Expression of GAD65 and Islet Cell Antibody (ICA512) Autoantibodies Among Cytoplasmic ICA+ Relatives Is Associated With Eligibility for the Diabetes Prevention Trial-Type 1", Diabetes, vol. 50, No. 8, Aug. 2001, pp. 1735-1740.
Lenschow et al., "Differential effects of anti-B7-1 and anti-B7-2 monoclonal antibody treatment on the development of diabetes in the nonobese diabetic mouse", J Exp Med., vol. 181, 1995, pp. 1145-1155.
Lan et al., "Molecular Cloning and Identification of a Receptor-Type Protein Tyrosine Phosphatase, IA-2, from Human Insulinoma", DNA Cell Biology, 1994, vol. 13, No. 5, pp. 505-514.
Lan et al., "Discrete Sequential Boundaries for Clinical Trials", Biometrika, Dec. 1983, vol. 70, No. 3, pp. 659-663.
Kretowski et al., "[Evaluation of helper T lymphocyte subpopulations: naive (CD4+CD45RA+), memory KCD4+CD45RO+) and co-expression of phenotypes CD45RA+ and CD45RO+ in preclinical phases of diabetes type 1 (prediabetes)]", Przeglag Lekarski, 2001, vol. 58, No. 1, pp. 16-19.
Keller et al., "Insulin prophylaxis in individuals at high risk of type I diabetes", Lancet, Apr. 1993, vol. 341(8850), pp. 927-938.
Kasimiotis et al., "Sex-determining region Y-related protein SOX13 is a diabetes autoantigen expressed in pancreatic islets", Diabetes, Apr. 2000, vol. 49, No. 4, pp. 555-561.
Kanegane et al., "Expression of L-selectin (CD62L) discriminates Th1- and Th2-like cytokine-producing memory CD4+ T cells", Immunology, Feb. 1996, vol. 87, No. 2, pp. 186-190.
Japanese Office Action for Application No. 2015-520517, dated Oct. 3, 2017, 7 pages.
Japanese Office Action for Application No. 2015-514216, dated Apr. 4, 2017, 7 pages.
Janeway et al., "The Immune System in Health and Disease", Immunobiology, 6th Edition, 2005, p. 452, Figure 10.35.
Jackson et al., "Institutional Policies and Guidelines on Adjuvants and Antibody Production", ILAR Journal, vol. 37, 1995, pp. 141-152.
InvivoGen (2011-2016) Vaccine Adjuvant: Incomplete Freund's adjuvant (2 pages). Accessed online at http://www.invivogen.com/ifa on Aug. 25, 2017).
Intravenous CTILA4-Jg Treatment in Resent Onset Type 1 diabetes Mellitus. Clinical Trials.gov Identifier: NCT00505375. Retrieved from the Internet:URL:http//:clinicaltrials.gov/ctl/show/NCT00505375, pp. 1-4.
International Search Report and Written Opinion received for PCT Patent Application No. PCT/US2013/048237, dated Oct. 18, 2013, 5 pages.

International Search Report and Written Opinion for Application No. PCT/US2013/048247, dated Oct. 18, 2013, 6 pages.
International Search Report and Written Opinion for Application No. PCT/US2013/042627, dated Sep. 12, 2013, 7 pages.
International Preliminary Report on Patentability received for PCT Patent Application No. PCT/US2013/48237, dated Jan. 8, 2015, 5 pages.
Huurman et al., "Differential inhibition of autoreactive memory- and alloreactive naive T cell responses by soluble cytotoxic T lymphocyte antigen 4 (sCTLA4), CTLA4Ig and LEA29Y", Clinical and Experimental Immunology, 2007, vol. 150, No. 3, pp. 487-493.
Hunter et al., "Adjuvant activity of non-ionic block copolymers. IV. Effect of molecular weight and formulation on titre and isotype of antibody", Vaccine, vol. 9, No. 4,1991, pp. 250-256.
Guy B., "The perfect mix: recent progress in adjuvant research", Nature Reviews Microbiology, vol. 5, 2007, pp. 505-517.
Glinka et al., "Protective regulatory T cell generation in autoimmune diabetes by DNA covaccination with islet antigens and a selective CTLA-4 ligand" Mol. Ther. Oct. 2006. vol. 14, No. 4, pp. 578-587.
Genant et al., "Abatacept inhibits progression of structural damage in rheumatoid arthritis: results from the long-term extension of the AIM trial", Ann Rheum Dis. Aug. 2008, vol. 67, No. 8, pp. 1084-1089.
Fukai et al., "The role of costimulatory molecules B7-1 and B7-2 in mice with experimental autoimmune uveoretinitis" Graefe's Archive for Clinical and Experimental Ophthalmology, Oct. 1999, vol. 237, Issue 11, pp. 928-933.
Extended European Search Report for Application No. 13810575.4, dated Feb. 1, 2016, 8 pages.
Extended European Search Report for Application No. 13810467.4, dated Apr. 28, 2016, 8 pages.
Extended European Search Report for Application No. 13794110.0, dated May 3, 2016, 8 pages.
European Search Report and Search Opinion Received for EP Application No. 13810575.4, dated Feb. 1, 2016, 7 pages.
Elias et al., "Induction of diabetes in standard mice by immunization with the p277 peptide of a 60-kDa heat shock protein", Eur. J. Immunol., vol. 25, No. 10, 1995, pp. 2851-2857.
Driessens et al.,"Costimulatory and coinhibitory receptors in antitumor immunity", Immunol. Rev. 2009, vol. 229, No. 1 pp. 126-144.
Dotta et al., "Autoimmunity to the GM2-1 islet ganglioside before and at the onset of type 1 diabetes", Diabetes, vol. 45, No. 9, 1996, pp. 1193-1196.
Dion Is 1 et al., "Target antigens in autoimmune diabetes: pancreatic gangliosides", Ann Isl Super Sanita, vol. 33, No. 3, 1997, pp. 433-435.
Davenport, F. M., "Seventeen years' experience with mineral oil adjuvant influenza virus vaccines", Ann Allergy, vol. 26, No. 6, 1968, pp. 288-292.
Christgau et al., "Pancreatic beta cells express two autoantigenic forms of glutamic acid decarboxylase, a 65-kDa hydrophilic form and a 64-kDa amphiphilic form which can be both membrane-bound and soluble", J Biol Chem, Nov. 5, 1991, vol. 266, No. 31, pp. 21257-21264.
Chittasupho et al., "Autoimmune therapies targeting costimulation and emerging trends in multivalent therapeutics", Ther. Deliv. Jul. 2011, 2(7), pp. 873-889.
Chinese Office Action for Application No. 201380034880.8, dated Jan. 13, 2016, 15 pages.
Chinese Office Action for Application No. 201380034847.5, dated Jan. 25, 2016, 14 pages.
Chinese Office Action for Application No. 201380027247.6, dated Nov. 4, 2015, 17 pages.
Chatenoud et al., "Clinical immunologic interventions for the treatment of type 1 diabetes", Cold Spring Harb Perspect Med., Aug. 1, 2012, vol. 2, No. 8, 19 pages.
Castano et al., "Identification and Cloning of a Granule Autoantigen (Carboxypeptidase-H) Associated with Type I Diabetes", Journal of Clinical Endocrinology & Metabolism vol. 73, No. 6, 1991, pp. 1197-1201.

(56) References Cited

OTHER PUBLICATIONS

Boitard et al., "Peripherin: an islet antigen that is cross-reactive with nonobese diabetic mouse class II gene products", PNAS, vol. 89, No. 1, 1992, pp. 172-176.
Bluestone et al., "CTLA4Ig: bridging the basic immunology with clinical application", Immunity, May 2006, vol. 24, No. 3, pp. 233-238.
Blazar et al., "Infusion of anti-B7.1 (CD80) and anti-B7.2 (CD86) monoclonal antibodies inhibits murine graft-versus-host disease lethality in part via direct effects on CD4+ and CD8+ T cells", J. Immunol, Oct. 1996, vol. 157, No. 8, pp. 3250-3259.
Bingley et al., "Combined analysis of autoantibodies improves prediction of IDDM in islet cell antibody-positive relatives", Diabetes, Nov. 1994, vol. 43, No. 11, pp. 1304-1310.
Beebe et al., "Long-term mortality follow-up of Army recruits who received adjuvant influenza virus vaccine in 1951-1953", Am. J. Epidemiol., vol. 95, No. 4, 1972, pp. 337-346.
American Diabetes Association, "Standards of Medical Care in Diabetes—2011", Diabetes Care, vol. 34 Suppl. 1, 2011, pp. S11-S61.
Aly et al., "Immunotherapeutic Approaches to Prevent, Ameliorate, and Cure Type 1 Diabetes", Am. J. Therapeutics, 2005, vol. 12, Issue 6, pp. 481-490.
Allison et al., "Immunological adjuvants: desirable properties and side-effects", Mol Immunol, Mar. 1991, vol. 28, No. 3, pp. 279-284.
Alcalde et al., "Cloning of Candidate Autoantigen Carboxypeptidase H from a Human Islet Library: Sequence Identity with Human Brain CPH", Journal of Autoimmunity, vol. 9, Issue 4, Aug. 1996, pp. 525-528.
Agresti, Categorical Data Analysis, New York, New York, John Wiley and Sons, Chapter 3, 1990, pp. 36-78.
Abrams et al., "CTLA4Ig-mediated blockade of T-cell costimulation in patients with psoriasis vulgaris", J Clin Invest., May 1999, vol. 103, No. 9, pp. 1243-1252.
Aanstoot et al., "Identification and characterization of glima 38, a glycosylated islet cell membrane antigen, which together with GAD65 and IA2 marks the early phases of autoimmune response in type 1 diabetes", J Clin Invest, vol. 97. No. 12, 1996, pp. 2772-2783.
[No Author Listed] Diabetes Control and Complications Trial Research Group., "The effect of intensive treatment of diabetes on the development and progression of long-term complications in insulin-dependent diabetes mellitus", N Engl J Med., Sep. 1993, vol. 329, No. 14, pp. 977-986.
Zhang, et al., "Acute response of peripheral blood cell to autologous hematopoietic stem cell transplantation in type 1 diabetic patient", PLoS One., 2012 Vol. 7, No. 2, Feb. 22, 2012.
Zhang et al., "Autoantibodies to IA-2 in IDDM: Location of Major Antigenic Determinants", Diabetes 1997, vol. 46, No. 1, pp. 40-43.
Yu et al., "DPT-1 Participating Investigators. Expression of GAD65 and islet cell antibody (ICA512) autoantibodies among cytoplasmic ICA+ relatives is associated with eligibility for the Diabetes Prevention Trial-Type 1. Diabetes", Aug. 2001, vol. 50, No. 8, pp. 1735-1740.
Xie et al., "Autoantibodies to IA-2 and IA-2 beta in insulin-dependent diabetes mellitus recognize conformational epitopes: location of the 37- and 40-kDa fragments determined", J. Immunol., vol. 159, No. 7, 1997, pp. 3662-3667.
Vincenti et al., "Costimulation Blockade with Belatacept in Renal Transplantation", N. Engl. J. Med., vol. 353, No. 8, 2005, pp. 770-781.
Verge et al., "Prediction of type 1 diabetes in first-degree relatives using a combination of insulin GAD and ICA512bdc/IA-2 autoantibodies", Diabetes, vol. 45, 1996, pp. 926-933.
Verge et al., "Combined use of autoantibodies (IA-2 autoantibody, GAD autoantibody, insulin autoantibody, cytoplasmic islet cell antibodies) in type 1 diabetes: Combinatorial Islet Autoantibody Workshop", Diabetes, vol. 47, 1998, pp. 1857-1866.
U.S. Appl. No. 15/185,831, filed Jun. 17, 2016, Diabetes Biomarkers.

U.S. Appl. No. 15/121,273, filed Aug. 24, 2016, Immunomodulatory Therapy for Type 1 Diabetes Mellitus Autoimmunity.
Turner et al., "HIV-1 immunogen induction of HIV-1 specific delayed-type hypersensitivity", AIDS, vol. 8, 1994, pp. 1429-1435.
Trauger et al., "Safety and immunogenicity of a gp120-depleted, inactivated HIV-1 immunogen: results of a double-blind, adjuvant collrolled trial", J Acquir Immune Defic Syndr Hum Retrovirol, vol. 10, Supp. 2, 1995, pp. S74-S82.
Trauger et al., "Effect of immunization with inactivated gp120-depleted human immunodeficiency virus type 1 (HIV-1) immunogen on HIV-1 immunity, viral DNA, and percentage of CD4 cells", J Infect Dis, vol. 169, 1994, pp. 1256-1264.
Tihamer Orban et al., "Co-stimulation modulation with abatacept in patients with recent-onset type 1 diabetes: a randomised, double-blind, placebo-controlled trial", The Lancet, vol. 378, No. 9789, Jul. 1, 2011 (Jul. 1, 2011), pp. 412-419.
Tanbara, K., "Angiogenesis therapy for ischemic cardiomyopathy. Utility of basic fibroblast growth factor sustained release system", Japanese-Language Article, History of Medicine, 1st Saturday Special Issue New Treatment Strategy for Heart Failure, New Treatment Target, 2003, vol. 206, Issue 10, pp. 824-828.
Tagami et al., "Ganglioside GM3 participates in the pathological conditions of insulin resistance", J Biol Chem., vol. 277, No. 5, 2002, pp. 3085-3092.
Swiniarski et al., "Immune Response Enhancement by in Vivo Administration of B7.2Ig, a Soluble Costimulatory Protein", Clinical Immunology, vol. 92, No. 3, 1999, pp. 235-245.
Sturmhoefel et al., "Potent Activity of Soluble B7-IgG Fusion Proteins in Therapy of Established Tumors and as Vaccine Adjuvant", Cancer research, Oct. 1999, vol. 59, No. 19, pp. 4964-4972.
Schneider et al., "Combination therapy with lnsB9-23 peptide immunization and CTLA4-IgG does not reverse diabetes in NOD mice", Clin. Immunol., vol. 142, No. 3, 2012, pp. 402-403.
Schengrund et al., "Gangliosides: glycosphingolipids essential for normal neural development and function", Trends Biochem. Sci. Jul. 2015, vol. 40, No. 7, pp. 397-406.
Sanderson et al., "Autoimmunity in a phase I trial of a fully human anti-cytotoxic T-lymphocyte antigen-4 monoclonal antibody with multiple melanoma peptides and Montanide ISA 51 for patients with resected stages III and IV melanoma", J. Clin. Oncol., Feb. 2005, vol. 23, No. 4, pp. 741-750.
Salk et al., "Control of influenza and poliomyelitis with killed virus vaccines", Science, vol. 195, No. 4281, 1977, pp. 834-847.
Ruperto et al., "Abatacept in children with juvenile idiopathic arthritis: a randomised, double-blind, placebo-controlled withdrawal trial", Lancet, vol. 372, No. 9636, 2008, pp. 383-391.
Roep, "The role of T-cells in the pathogenesis of Type 1 diabetes: from cause to cure", Diabetologia., Mar. 2003, vol. 46, No. 3, pp. 305-321.
Rigby et al., "CD28/CD154 Blockade Prevents Autoimmune Diabetes by Inducing Nondeletional Tolerance After Effector T-Cell Inhibition and Regulatory T-Cell Expansion", Diabetes, vol. 57, No. 10, Oct. 2008, pp. 2672-2683.
Ramiya, et al. "Antigen Based Therapies to Prevent Diabetes in NOD Mice," Journal of Autoimmunity Jun. 1996, vol. 9, No. 3, pp. 349-356.
Rabin et al., "Islet cell antigen 512 is a diabetes-specific islet autoantigen related to protein tyrosine phosphatases", J. Immunol., vol. 152, No. 6, 1994, pp. 3183-3188.
Pozzilli et al., "Immunotherapy for Type 1 diabetes: getting beyond a negative first impression", Immunotherapy, Jul. 2012, vol. 4, No. 7 pp. 655-658.
Pietropaolo et al., "Islet cell autoantigen 69 kD (ICA69). Molecular cloning and characterization of a novel diabetes-associated autoantigen", J Clin Invest., 1993, vol. 92, No. 1, pp. 359-371.
Phillips et al., "Current state of type 1 diabetes immunotherapy: incremental advances, huge leaps, or more of the same?", Clin. Dev Immunol. 2011;2011:432016. doi: 10.1155/2011/432016, Epub Jul. 18, 2011. 18 pages.
Palmer et al., "C-peptide is the appropriate outcome measure for type 1 diabetes clinical trials to preserve beta-cell function: report of an ADA workshop, Oct. 21-22, 2001", Diabetes, Jan. 2004, vol. 53, No. 1, pp. 250-264.

(56) References Cited

OTHER PUBLICATIONS

Orban et al., Diabetes, vol. 48, Suppl. 1, 1999, p. A216.
Muir et al., "Antigen-specific immunotherapy: oral tolerance and subcutaneous immunization in the treatment of insulin-dependent diabetes", Diabetes Metab. Rev., vol. 9, No. 4, 1993, pp. 279-287.
Muir et al., "Insulin immunization of nonobese diabetic mice induces a protective insulitis characterized by diminished intraislet interferon-gamma transcription", J Clin Invest., Feb. 1995, vol. 95, No. 2, pp. 628-634.
Mueller, M., et al., "Tumor eradication by immunotherapy with biodegradable PLGA microspheres—an alternative to Incomplete Freund's adjuvant" Int. J. Cancer, Jul. 15, 2011, vol. 129, No. 2, pp. 407-416.
Mehling et al., "FTY720 therapy exerts differential effects on T cell subsets in multiple sclerosis", Neurology, Oct. 14, 2008, vol. 71, No. 16, pp. 1261-1267.
Mease et al., "Abatacept in the treatment of patients with psoriatic arthritis: results of a six-month, multicenter, randomized, double-blind, placebo-conliolled, phase II trial", Arthritis Rheum, Apr. 2011, vol. 63, No. 4, pp. 939-948.
McDevitt et al., "Specific antigen vaccination to treat autoimmune disease" Proc. Natl. Acad. Sci. USA. Oct. 5, 2004, 101 Suppl 2, pp. 14627-14630.
Mayo Foundation for Medical Education and Research, 2012, accessed at mayoclinic.com/health/type-1-diabetes/DS00329 on Sep. 13, 2012.
Matteucci, E., et al., Altered proportions of naive, central memory and terminally differentiated central memory subsets among CD4+ and CD8 + T cells expressing CD26 in patients with type 1 diabetes. J. Clin. Immunol., Dec. 2011, vol. 31, No. 6, pp. 977-984.
Abiru et al., "Dual Overlapping Peptides Recognized by Insulin Peptide B:9-23 T Cell Receptor AV13S3 T Cell Clones of the NOD Mouse," J Autoimmun, 2000, 14:231-237.
Chatenoud et al., "Clinical Immunologic Interventions for the Treatment of Type 1 Diabetes," Cold Spring Harb Perspect Med, Jun. 7, 2012, 2:a007716, 18 pp.
Lee et al., "Structure of a human insulin peptide-HLA-DQ8 complex and susceptibility to type 1 diabetes," Nat Immunol, Jun. 2001, 2(6):501-507.
Vadasz et al., "Abnormal deposition of collagen around hepatocytes in Wilson's disease is associated with hepatocyte specific expression of lysyl oxidase and lysyl oxidase like protein-2," J Hepatol, 2005, 43:499-507.
Austrialian Office Action dated Feb. 9, 2018 for Patent Application No. 2013266145.
Indian Office Action dated Aug. 22, 2019 for Patent Application No. 10259/DELNP/2014.
Indian Office Action dated Sep. 25, 2019 for Patent Application No. 215/DELNP/2015.
New Zealand Office Action dated Jun. 23, 2017 for Patent Application No. 703648.
Orban et al., "Reduction in CD4 central memory T-cell subset in costimulation modulator abatacept-treated patients with recent-onset type 1 diabetes is associated with slower C-peptide decline. Diabetes", Oct. 2014, vol. 63, No. 10, pp. 3449-3457.
Orban et al., "Prevention of Type 1 Diabetes Mellitus using a Novel Vaccine", Ther. Adv. Endocrinol Metab. Feb. 2011, vol. 2, No. 1, pp. 9-16.
Orban et al., "Autoantigen-specific regulatory T cells induced in patients with type 1 diabetes mellitus by insulin B-chain immunotherapy", J. Autoimmun., Jun. 2010, vol. 34, No. 4, pp. 408-415.
Office Action received for European Application No. 13810575.4, dated Feb. 2, 2017, 6 pages.
Office Action received for European Application No. 13810575.4 dated Sep. 14, 2018, 5 pages.
No Author Listed, "New Hope for immune therapy for children and Young Adults with Type 1 Diabetes: Founder of Orban Biotech's Landmark Findings for Abatacept Published in The Lancet", MarketWired, Aug. 5, 2011, 2 pages, Orban Biotech was the source of the information. Retrieved on Jan. 19, 2018 from <http://www.marketwired.com/press-release/new-hope-immune-therapy-children-young-adults-with-type-1-diabetes-founder-organ-biotechs-1546447.htm.
New Zealand Office Action for Application No. 703648, dated Jun. 7, 2017, 3 pages.
New Zealand Office Action for Application No. 703648, dated Jun. 21, 2016, 5 pages.
New Zealand Office Action for Application No. 703641, dated May 30, 2017, 4 Pages.
NCT00505375, ClinicalTrials.gov, Updated on Jan. 31, 2011.
Naid, et al. "Intravenous CTLA4-Ig Treatment in Recent Onset Type 1 Diabetes Mellitus," Clinical Trials.gov url: http://clinicaltrials.gov/ct2/show/record/NCT00505375?term=NCT00505375&rank=1, Feb. 9, 2013.
Canadian Office Action dated Oct. 21, 2021 for Patent Application No. 2,877,986.

* cited by examiner

CTLA4 FUSION PROTEINS FOR THE TREATMENT OF DIABETES

CROSS REFERENCE TO RELATED APPLICATIONS

This application is a continuation application of U.S. application Ser. No. 14/576,990 filed Dec. 19, 2014, which is a continuation of U.S. patent application Ser. No. 14/021,629 filed Sep. 9, 2013, which is a continuation of U.S. patent application Ser. No. 13/534,560 filed Jun. 27 2012, which are hereby incorporated by reference in their entirety.

FIELD OF THE INVENTION

The present invention relates generally to the field of autoimmune disease and specifically to the treatment, prevention, or delayed progression of Type 1 diabetes mellitus.

BACKGROUND

The most common form of Type 1 diabetes mellitus (T1DM) is an immune-mediated disease where insulin-secreting β-cells are destroyed by an autoimmune response. There are a number of genetic and environmental factors associated with the onset of the disease, which involves the progressive inflammatory infiltration of pancreatic islets containing immunocytes targeted specifically to insulin-secreting β-cells. This pathology develops over an indeterminate period of time (months to years). While the discovery of insulin allowed for the treatment of T1DM, there is currently no cure. The most common form of Type 1 diabetes mellitus is immune-mediated, in which insulin-producing β cells are destroyed. Yet, at the time of diagnosis, most patients still have appreciable amounts of insulin production. Preservation of residual β-cell function is highly desirable because it can reduce short-term and long-term complications of the disease.

Several clinical trials have been undertaken in an attempt to arrest autoimmunity in Type 1 diabetes with immunomodulatory agents or antigen-based treatments. Most notably, trials of anti-CD3, anti-CD20, and a GAD-65 antigen vaccine have shown some efficacy in preservation of β-cell function as evidenced by stimulated C-peptide secretion. T cells play a central part in autoimmunity associated with Type 1 diabetes.

However, there is need for additional new therapies for Type 1 diabetes mellitus that are able to halt or slow autoimmune β-cell destruction leading to preservation of β-cell function and C-peptide secretion, particularly in patients recently diagnosed with Type 1 diabetes.

SUMMARY

In accordance with certain embodiments of the present invention relate to a method of treating diabetes mellitus in a subject comprising administering an effective amount of a fusion protein composition comprising a T-cell co-stimulation antagonist and a portion of an immunoglobulin molecule.

In some embodiments, the T-cell co-stimulation antagonist comprises the extracellular domain of CTLA4, an effective fragment of the extracellular domain or immunologically active variant of the extracellular domain. The T-cell co-stimulation antagonist may bind a B7 antigen expressed on B cells or other antigen presenting cells (APCs). In some embodiments, the B7 antigen is expressed on B cells and on APCs.

In some embodiments, the fusion protein is Abatacept. In some embodiments, the composition further comprises an oil-based carrier such as a water-in-oil emulsion (e.g., IFA or Montamide ISA). The composition may be administered by intravenous infusion, such as in about 50 to 200 ml of physiological saline or at a dose ranging from about 5 mg/kg to about 50 mg/kg or at a dose ranging from about 250 to 2000 mg, or at a dose of 500 mg, 750 mg, or 1000 mg.

The methods as described herein may also comprise determining levels of C-peptide in blood samples taken from the subject over time as an indicator of effectiveness of the treatment in inhibiting activation of auto-aggressive T-cells. In some embodiments, the effectiveness of the composition in inhibiting activation of auto-aggressive T-cells is indicated by maintenance of C-peptide production or a delay in reduction of C-peptide production as compared to a standard or by improved HbA1c or reduction in the use of insulin by said subject as compared to a standard. Such measurements can be done ex vivo, such as by analyzing a blood sample. The reduction of C-peptide production in said subject may be delayed for at least 3, 6, 9, 12, or 18 months, or 2, 3, 4, or more years.

In some embodiments, a preferred patient population is treated. For example, a patient selected from a population having a statistically greater response rate, such as a white patient, is treated.

Some embodiments provided herewith provide a method of preventing the onset of diabetes in a subject at risk for diabetes mellitus comprising administering an effective amount of a fusion protein composition comprising a T-cell co-stimulation antagonist and a portion of an immunoglobulin molecule. Some embodiments provided herewith provide a method delaying the onset of diabetes by at least 3, 6, 9, 12, or 18 months, or 2, 3, 4, or more years in a subject at risk for diabetes mellitus by administering an effective amount of a fusion protein composition comprising a T-cell co-stimulation antagonist and a portion of an immunoglobulin molecule.

These and other features of the embodiments as will be apparent are set forth and described herein.

BRIEF DESCRIPTION OF THE DRAWINGS

A detailed description of various embodiments is provided herein below with reference, by way of example, to the following drawings. The skilled person in the art will understand that the drawings, described below, are for illustration purposes only. The drawings are not intended to limit the scope of the applicant's teachings in any way.

It will be understood that the drawings are exemplary only and that all reference to the drawings is made for the purpose of illustration only, and is not intended to limit the scope of the embodiments described herein below in any way.

DETAILED DESCRIPTION

It has been found that a CTLA4 molecule can be used for the treatment, prevention, or delayed progression of Type 1 diabetes mellitus (T1DM) in a subject.

Preservation of residual β-cell function (as measured by peak C-peptide ≥0.2 nmol/L) is highly desirable because it can reduce short-term and long-term complications of the disease. Several clinical trials have been undertaken in an attempt to arrest autoimmunity in Type 1 diabetes with immunomodulatory agents or antigen-based treatments. Most notably, trials of anti-CD3, anti-CD20, and a GAD-65 antigen vaccine have shown some efficacy in preservation of β-cell function as evidenced by stimulated C-peptide secretion. C-peptide is a protein that is produced in the body along with insulin. In a healthy pancreas, preproinsulin is secreted with an A-chain, C-peptide, a B-chain, and a signal sequence. The signal sequence is cut off, leaving proinsulin. Then the C-peptide is cut out, leaving the A-chain and B-chain to form insulin. Since C-peptide and insulin are present in equimolar amounts, it is a highly reliable marker for insulin production and the health of pancreatic β cells.

T cells play a central part in autoimmunity associated with Type 1 diabetes. To become fully activated and autoaggressive, T cells are believed to need at least two crucial signals. (Marelli-Berg F M, Okkenhaug K, Mirenda V. A *Trends Immunol* 2007; 28: 267-73.) The first signal is an interaction between an antigen in the groove of the MHC molecule on antigen-presenting cells and the T-cell receptor (TCR). The most important second signal is the interaction between CD80 and CD86 on the antigen presenting cells (APCs) and CD28 on the T cells. This costimulatory second signal is needed for full activation of cells, and without it T cells do not become functional. Therefore, co-stimulation blockade has been proposed as a therapeutic modality for autoimmunity and transplantation. (Bluestone J A, St Clair E W, Turka L A. *Immunity* 2006; 24: 233-38.)

Cytotoxic T-lymphocyte-associated antigen 4 (CTLA4), which is also known as CD152, is a protein involved in the regulation of the immune system. Naturally occurring CTLA4 is described in U.S. Pat. Nos. 5,434,131, 5,844,095, and 5,851,795. Natural CTLA4 proteins are encoded by the CTLA4 gene. CTLA4 is a cell surface protein, having an N-terminal extracellular domain, a transmembrane domain, and a C-terminal cytoplasmic domain. The extracellular domain binds to and/or interferes with target antigens, such as CD80 and CD86, serves as nature natural break of T cell stimulation. In some embodiments, the extracellular domain of the CTLA4 molecule begins with methionine at position +1 and ends at aspartic acid at position +124; in other embodiments, the extracellular domain begins with alanine at position −1 and ends at aspartic acid at position +124.

A CTLA4 molecule is a molecule comprising a cytotoxic T-lymphocyte-associated antigen 4 (CTLA4) extracellular domain. In some embodiments, the extracellular domain of CTLA4 comprises a portion of the CTLA4 protein that recognizes and binds to at least one B7 (CD80/86) antigens such as a B7 antigen expressed on B cells and APCs. The extracellular domain may also include fragments or derivatives of CTLA4 that bind a B7 antigen. The CTLA4 extracellular domain can also recognize and bind CD80 (B7-1) and/or CD86 (B7-2). The extracellular domain may also include fragments or derivatives of CTLA4 that bind a binds CD80 and/or CD86.

The CTLA4 molecule may be a fusion protein, where a fusion protein is defined as one or more amino acid sequences joined together using methods well known in the art. The joined amino acid sequences thereby form one fusion protein. In some embodiments, the CTLA4 molecule contains at least a portion of an immunoglobulin, such as the Fc portion of an immunoglobulin. In some embodiments, the CTLA4 molecule is an isolated and purified CTLA4 molecule.

In some embodiments, the CTLA4 molecule is a protein containing at least a portion of an immunoglobulin, such as the Fc portion of an immunoglobulin. In some embodiments, the CTLA4 molecule is an isolated and purified CTLA4 molecule.

In one preferred embodiment, the CTLA4 molecule is abatacept. Abatacept is a soluble fusion protein that consists of the extracellular domain of human CTLA-4 linked to the modified Fc (hinge, CH2, and CH3 domains) portion of human immunoglobulin G1 (IgG1). Abatacept is produced by recombinant DNA technology in a mammalian cell expression system. The apparent molecular weight of abatacept is 92 kilodaltons.

Abatacept was developed for use in adult rheumatoid arthritis and juvenile idiopathic arthritis and is indicated for reducing signs and symptoms, inducing major clinical response, inhibiting the progression of structural damage, and improving physical function in adult patients with moderately to severely active rheumatoid arthritis.

Abatacept was developed by Bristol-Myers Squibb and is disclosed, for example, in U.S. Pat. Nos. 5,851,795, 7,455, 835, and U.S. Pat. Pub. 20011/311529. Abatacept, under the trade name ORENCIA, may be used as monotherapy or concomitantly with disease-modifying antirheumatic drugs (DMARDs) other than tumor necrosis factor (TNF) antagonists. Abatacept is also indicated for reducing signs and symptoms in pediatric patients 6 years of age and older with moderately to severely active polyarticular juvenile idiopathic arthritis. Abatacept may be used as monotherapy or concomitantly with methotrexate (MTX). Since abatacept is a selective costimulation modulator and inhibits the costimulation of T cells, it should not be administered concomitantly with TNF antagonists.

Abatacept selectively binds to CD80 and CD86, thereby blocking the interaction with CD28 and interfering with T-cell activation. It inhibits naive T-cell activation, thus having the potential to selectively inhibit T-cell response to specific antigens instead of broad immunosuppression. Effector-memory T-cell responses are less dependent on CD28 co-stimulation and, presumably, are less inhibited by co-stimulation blockade. (Lo D J, Weaver T A, Stempora L, et al. *Am J Transplant* 2011; 11: 22-33.)

Studies in both animals and human beings have shown that interruption of the co-stimulatory second signal beneficially affects autoimmunity Co-stimulation blockade with abatacept has been shown to have clinical effectiveness in psoriasis (Abrams J R, Lebwohl M G, Guzzo C A, et al. *J Clin Invest* 1999; 103: 1243-52) and psoriatic arthritis (Mease P, Genovese M C, Gladstein G, et al. *Arthritis Rheum* 2011; 63: 939-48) and is approved for treatment of rheumatoid arthritis, Genant H K, Peterfy C G, Westhovens R, et al. *Ann Rheum Dis* 2008; 67: 1084-89) including juvenile rheumatoid arthritis. (Ruperto N, Lovell D J, Quartier P, et al *Lancet* 2008; 372: 383-91.) Additionally, co-stimulation blockade has been effective in control of allograft rejection. (Vincenti F, Larsen C, Durrbach A. *N Engl J Med* 2005; 353: 770-81.) Moreover, Lenschow and coworkers (Lenschow D J, Ho S C, Sattar H, et al. *J Exp Med* 1995; 181: 1145-55) showed that costimulatory blockade with both an anti B7-2 monoclonal antibody and a CTLA4-immunoglobulin fusion protein prevented diabetes in the NOD mice model when administered prior to 10 weeks of age.

It has now been shown that co-stimulation modulation with T-cell co-stimulatory antagonists such as CTLA-4 compositions and in particular abatacept, halts or slows autoimmune β-cell destruction leading to preservation of C-peptide secretion in recently diagnosed patients with Type 1 diabetes by blocking the generation of autoaggressive T cells (Orban et al., *Lancet* 2011; 378 (9789): 412-9.)

Thus, there is provided herein a method of treating, preventing, or delaying the progression of diabetes mellitus by administering a CTLA4 molecule. The methods of the invention can prevent or delay the onset of diabetes mellitus, or prevent or delay loss of residual β-cell mass, providing a longer remission period and delaying the onset of diabetes-related complications at a later stage of the life.

T1DM may be treated by the methods as described herein. The treatment can be for subjects with residual beta-cell function as well as for those no longer having any beta-cell function. The treatment may also be suggested for subjects provided exogenous beta-cells through transplant or injection or other beta cell replacement modalities (like embryonic or other stem cell therapies or other replacement modalities).

T1DM may be prevented in a subject by first selecting a subject who is susceptible to developing diabetes and administering a CTLA4 molecule as described herein. The subject who is susceptible to developing diabetes may be selected by the expression of one or more of: GAD65 autoantibodies (GAAs), ICA512 autoantibodies (ICA512AAs), or anti-insulin autoantibodies (IAAs). Each of these autoantibodies is associated with a risk of progression to autoimmune Type 1 diabetes. Expression of two or more of: GAD65 autoantibodies (GAAs), ICA512 autoantibodies (ICA512AAs), or anti-insulin autoantibodies (IAAs) is associated with a high risk of progression to autoimmune Type 1 diabetes. (Liping Yu et al., *Diabetes* August 2001 vol. 50 no. 8 1735-1740; Verge C F et al., *Diabetes* 45:926-933, 199; Verge C F. et al, *Diabetes* 47:1857-1866, 1998; and Bingley P J, et al., *Diabetes* 43:1304-1310, 1994).

The onset of T1DM may be delayed by the methods as described herein such that insulin is not needed by the subject for a longer length of time. Alternatively or in addition, the present method may extend the "honeymoon phase" in an already diabetic subject. The honeymoon phase is where insulin is secreted by the pancreas, causing high blood sugar levels to subside, and resulting in normal or near normal glucose levels due to responses to insulin injections and treatment.

The CTLA4 molecules as described herein may be administered in combination with a pharmaceutically acceptable carrier and administered as a pharmaceutical composition. The term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical-Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of provided herein, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds described herein including pharmaceutically acceptable carriers can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compositions as described herein may be administered with an adjuvant. The term "adjuvant" can be a compound that lacks significant activity administered alone but can potentiate the activity of another therapeutic agent. In some embodiments, an adjuvant is selected from the group consisting of buffers, anti-microbial preserving agents, surfactants, antioxidants, tonic regulators, antiseptics, thickeners and viscosity improvers. In some embodiments, the adjuvant is IFA or other oil-based adjuvant is present between 30-70%, preferably between 40-60%, more preferably between 45-55% proportion weight by weight (w/w). In some embodiments, CTLA4 and IFA or other oil based adjuvant are present in about a 50/50 weight by weight ratio. In some embodiments, the pharmaceutical composition is free of contaminants, e.g., pyrogens.

For oral administration, the compound can be formulated readily by combining the CTLA4 molecule with one or more pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired. to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

The compound may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate. Thus, in some embodiments, the composition may be a water-in-oil emulsion. In other embodiments, the composition may be an oil-in-water emulsion. Such oil-in-water emulsions may be particularly useful for controlling the release profile and providing a slow release of the active drug, which can potentially be absorbed unaltered from such an emulsion.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer. Alternatively, the active ingredient may be in powder form for constitution with a suitable vehicle, e.g., sterile pyrogen-free water, before use.

In some embodiments, the composition comprising a CTLA4 molecule also includes an oil-based carrier.

The oil-based carrier is a composition that includes at least 10% by weight of a natural or synthetic oil suitable for administration to a human in conjunction with a therapeutic agent. In preferred embodiments, the carrier includes at least 20, 30, 50, 70, 80, 90, 95, 98, or 99% oil by weight. In some embodiments, the oil-based carrier can include less than 70, 60, 50, 40, 30 or 20% oil by weight. In preferred embodiments, the oil will be in the range of 10 to 95%, preferably 20 to 90% or 30 to 70% oil by weight. The oil should be chosen such that it provides for sustained release of a substance dispersed within it when administered to a subject. Suitable oils include mineral oil (e.g., Drakeol 6 VR light mineral oil), vegetable oil, squalene, or liquid paraffin. In some embodiments, the oil-based carrier can contain more than one type of oil. In some embodiments, the oil-based carrier can include an immune stimulator, e.g., an immunostimulating glucan, but it is much preferred that the oil-based carrier does not include an immune stimulator, e.g., an immunostimulating glucan, a bacterial component, e.g., a mycobacterial component. In a preferred embodiment, the oil-based carrier does not include an alum component.

While not wanting to be bound by theory, an oil based carrier is believed to work by triggering the immunocompetent cells, which are related to the inflammatory as well as protective ability. An oil-based carrier can also act as an antigen vehicle and a slow release or long-term antigen presentation device. When injected into a subject, an oil-based carrier and antigen composition can form a depot of antigen at the injection site, thereby protecting the antigen from degradation. From this depot the antigen can be released slowly into the system and provides a prolonged antigen presentation as well as expanded total contact surface area and the attraction of inflammatory cells. Macrophages can digest most of the incorporated materials and present the processed antigens on their surface. From this depot the antigen can be released slowly into the system and provides a prolonged antigen supply to act as costimulatory modulator.

Oil based carriers optionally include an emulsifier or surfactant component. The emulsifier or surfactant (and the amount of emulsifier or surfactant) is chosen such that it facilitates the mixture or dispersion of a substance, e.g., an antigen preparation, with the oil. An oil-based carrier can include 0.1 to 50%, preferably 1 to 30%, more preferably 5 to 20% by weight of a surfactant or emulsifier. Examples of emulsifiers or surfactants include Arlacel A, mannide oleate (e.g., Montamide 80-mannide monooleate), anhydrous mannitol/oleic acid ester, polyoxyethylene or polyoxypropylene.

An oil-based carrier or adjuvant typically consists of two components: (1) an oil, and (2) an emulsifier or surfactant, mixed with water. Suitable oils and emulsifiers are known in the art. For example, the oil can be mineral oil, vegetable oil, squalene or liquid paraffin. The emulsifier or surfactant can be, e.g., Arlacel A, mannide oleate, anhydrous mannitol/oleic acid ester, polyoxyethylene or polyoxypropylene. Exemplary oil-based adjuvants include conventional IFA, Montamide ISA adjuvants, or Hunter's TiterMax adjuvant. In preferred embodiments, the adjuvant includes 20 to 95%, preferably 30 to 90%, more preferably 40 to 70% by weight of an oil phase, and 0.1 to 50%, preferably 1 to 30%, more preferably 5 to 20% by weight of a surfactant or emulsifier. Various types of oil-based adjuvants are described, e.g., in U.S. Pat. Nos. 5,814,321, 6,299,884, 6,235,282, and 5,976,538.

IFA is typically a mixture of a non-metabolizable oil (e.g., mineral oil), water, and a surfactant (e.g., Arlacel A). Unlike Complete Freund's Adjuvant (CFA), IFA does not contain a bacterial component, e.g., mycobacteria. The first large-scale vaccinations using IFA in humans took place on US military personnel (Davenport (1968) Ann Allergy 26:288-292; Beebe et al., (1972) Am J Epidemiol 95:337-346; Salk & Salk (1977) Science 195:834-847). The findings were essentially negative with respect to malignancy, allergic diseases and collagenosis, but there was evidence that some men had a cyst like reaction at the site of inoculation. Follow up studies showed that these adverse events were due to improper administration of the compound, i.e. it was given s.c. instead of i.m. From these experiments, IFA was regarded by some as unsuitable for human purposes, although it has remained widely used in animal research. In recent years, newer forms of IFA have been shown safe for human use in HIV immunotherapy or therapeutic vaccinations (Turner et al. (1994) AIDS 8:1429-1435; Trauger et al. (1995) J Acquir Immune Defic Syndr Hum Retrovirol 10 Supp2:S74-82; Trauger et al. (1994) J Infect Dis 169:1256-1264).

Montanide ISA Adjuvants (Seppic, Paris, France) are a group of oil/surfactant based adjuvants in which different surfactants are combined with either a non-metabolizable mineral oil, a metabolizable oil, or a mixture of the two. They are prepared for use as an emulsion with aqueous Ag solution. The surfactant for Montanide ISA 50 (ISA=Incomplete Seppic Adjuvant) is mannide oleate, a major component of the surfactant in Freund's adjuvants. The surfactants of the Montanide group undergo strict quality control to guard against contamination by any substances that could cause excessive inflammation, as has been found for some lots of Arlacel A used in Freund's adjuvant. The various Montanide ISA group of adjuvants are used as water-in-oil emulsions, oil-in-water emulsions, or water-in-oil-in-water emulsions. The different adjuvants accommodate different aqueous phase/oil phase ratios, because of the variety of surfactant and oil combinations.

Hunter's TiterMax (CytRx Corp., Norcross, Ga.) is an oil/surfactant-based adjuvant prepared as a water-in-oil emulsion in a manner similar to that used for conventional Freund's adjuvants. However, it uses a metabolizable oil (squalene) and a nonionic surfactant that has good protein antigen-binding capacity as well as adjuvant activity. The adjuvant activity may relate, in part, to the surfactant's ability to activate complement and bind complement components, as this helps target the Ag to follicular dendritic cells in the spleen and lymph nodes. The surfactant used in the commercially available adjuvant is one of a number of synthetic nonionic block copolymers of polyoxyethylene and polyoxypropylene developed by Hunter (Hunter et al., 1991 Vaccine 9:250-256). The utilization of copolymer-coated microparticles to stabilize the emulsion permits formation of stable emulsions with less than 20% oil, an important factor in minimizing total adjuvant injected.

An adjuvant can be used with antigens to elicit cell-mediated immunity and the production of antibodies of protective isotypes (IgG2a in mice and IgG1 in primates). Different types of adjuvants share similar side effects, such as a reaction at the injection site and pyrogenicity. Alum, a commonly used adjuvant for human vaccine also produces an appreciable granulomatous response at the injection site (Allison & Byars (1991) Mol Immunol 28:279-284). The mode of action of an incomplete Freund's adjuvant can involve non-specific as well as specific immune responses. IFA seems to work by triggering the immunocompetent cells, which are related to the inflammatory as well as protective ability. IFA also acts as an antigen vehicle and a slow release or long-term antigen presentation device. Injecting a patient with an IFA and antigen compound, it forms a depot of antigen at the injection site, thereby protecting the antigen from degradation. From this depot the antigen is released slowly into the system and provides a prolonged antigen presentation as well as expanded total contact surface area and the attraction of inflammatory cells. Macrophages digest most of the incorporated materials and present the processed antigens on their surface. From this depot the antigen can be released slowly into the system and provides a prolonged antigen supply to act as costimulatory modulator.

The specific enhancing effect of the IFA on the antigen immunogenicity has been found to lead to increased humoral immunity (preferentially protective antibody production; IgG1 in humans and IgG2a in mice) and to elicit specific cell mediated immunity (preferentially Th2 type). Specifically, as an example human recombinant insulin B-chain in IFA results in Th2 cytokine pattern in NOD mice islets (Ramiya et al. (1996) J Autoimmun 9. 349-356). IFA is unique among adjuvants tried for diabetes prevention in animal models. Ramiya and coworkers (supra) concluded that both alum and DPT as adjuvants have 'non-specific' protective effects unrelated to the antigen used, while IFA is the only one with antigen specific protective effect for diabetes prevention in animals.

IFA, preferably an IFA approved for human use, e.g., Montanide (e.g., Montanide ISA51, Seppic Inc., France) or an equivalent composition, is a preferred adjuvant for use in the methods and vaccines described herein. Montanide ISA51 has shown no systemic or significant local side effects in our animal and in our human studies.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired. to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

The compounds may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer. Alternatively, the active ingredient may be in powder form for constitution with a suitable vehicle, e.g., sterile pyrogen-free water, before use.

The amount of the combination of a CTLA4 molecule provided to the subject will depend on both the size and weight of the subject as well as the progression of the disease. For the compounds described herein, the therapeutically effective amount can be initially determined from in vitro assays. Since the compounds of the present invention may have a low absorption and low bioavailability, the therapeutically effective amount may be determined from, for example, blood level of the compounds or metabolites thereof or fecal concentration of the compounds or metabolites thereof. As is well known in the art, therapeutically effective amounts for use in humans can also be determined from animal models. A therapeutically effective dose can also be determined from human data for compounds which are known to exhibit similar pharmacological activities. The applied dose can be adjusted based on the relative potency of the administered compound as compared with the known compound.

Patient doses for parenteral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

The CTLA4 molecule may be administered in a single daily dose or it may be administered multiple times per day. Alternatively, it may be administered less than once a day. The dosing may be over a period of time, such as once a month, or every 28 days. In some embodiments, additional doses (e.g., bolus dosing) may be given at the beginning of treatment. In some embodiments, a dose containing approximately 5, 10, 20, 30, 50, 100 mg/kg of the CTLA4 molecule.

The definitions of terms used herein are meant to incorporate the present state-of-the-art definitions recognized for each term in the chemical and pharmaceutical fields. Where appropriate, exemplification is provided. The definitions apply to the terms as they are used throughout this specification, unless otherwise limited in specific instances, either individually or as part of a larger group.

As used herein, the terms "administering" or "administration" are intended to encompass all means for directly and indirectly delivering a compound to its intended site of action.

The phrase "delaying the progression" as used herein in the context of delaying the progression of diabetes mellitus means that the loss of functional residual β-cell mass, after the clinical onset of Type 1 diabetes is delayed. The delayed progression of T1DM can be measured, for example, by measuring C-peptide production.

The phrase "pharmaceutically acceptable" refers to additives or compositions that are physiologically tolerable and do not typically produce an allergic or similar untoward reaction, such as gastric upset, dizziness and the like, when administered to an animal, such as a mammal (e.g., a human). The term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's, The Science and Practice of Pharmacy, (Gennaro, A. R., ed., $19^{th}$ edition, 1995, Mack Pub. Co.), discloses various carriers used in formulating pharmaceutical compositions and known techniques for the preparation thereof. Except insofar as any conventional carrier medium is incompatible with the compounds of provided herein, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc. Excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "pharmaceutical composition" refers to a composition described herein, or pharmaceutically acceptable salts thereof, with other agents such as carriers and/or excipients. Preferably, a pharmaceutical composition will have the active agent present at least 95% purity, or 98% purity, or 99% purity, or more.

As used herein, the term "subject" is a human or other animal, having a diabetes, pre-diabetes, or a predisposition to diabetes. Thus, in some embodiments the subject will be in need of the therapeutic treatment as provided herein. Preferred patients are mammals. Examples of patients include but are not limited to, humans, horses, monkeys, dogs, cats, mice, rates, cows, pigs, goats and sheep. In some embodiments, "subjects" are generally human patients having diabetes. In some embodiments, "subjects" are human patients who have been diagnosed with T1DM within the last 200, 100, or 50 days. In some embodiments, "subjects" are human patients who have been recently diagnosed with diabetes mellitus but still have residual beta-cell function. In some such embodiments the residual beta-cell function is detectable or at least 10%, 20%, 30%, 40%, 50%, 60%, or more of the beta cells in a fully functioning pancreas.

The term "therapeutically effective amount" refers to an amount effective, at dosages and for periods of time necessary, to achieve the desired biological or medicinal response in a cell culture, tissue system, animal, or human (e.g, the desired therapeutic result). A therapeutically effective amount of the composition may vary according to factors such as the disease state, age, sex, and weight of the individual, and the ability of the CTLA4 molecule to elicit a desired response in the individual. A therapeutically effective amount is also one in which any toxic or detrimental effects of the pharmacological agent are outweighed by the therapeutically beneficial effects. In some embodiments, the response includes alleviation and/or delay of onset of one or more symptoms of the disease, condition, or disorder being treated.

The term "treatment" or "treating" as used herein is defined as the application or administration of the therapeutic agents to a subject, or application or administration of the therapeutic agents to an isolated tissue or cell line from a subject who has diabetes, a symptom of disease or a predisposition toward a disease. Treatment is intended to encompass preventing the onset, slowing the progression, reversing or otherwise ameliorating, improve, or affect the disease, the symptoms or of disease or the predisposition toward disease. For example, treatment of a subject, e.g., a human subject, with a composition described herein, can slow, improve, or stop the ongoing autoimmunity, e.g., a reaction against pancreatic β-cells, in a subject before, during, or after the clinical onset of Type 1 diabetes.

The term "about" or "approximately" means within an acceptable error range for the particular value as determined by one of ordinary skill in the art, which will depend in part on how the value is measured or determined—e.g., the limitations of the measurement system, or the degree of precision required for a particular purpose. For example, "about" can mean within 1 or within 2 standard deviations, as per the practice in the art. Alternatively, "about" can mean a range of up to 20%, preferably up to 10%, and more preferably up to 5% of a given value. Where particular values are described in the application and claims, unless otherwise stated, the term "about" meaning within an acceptable error range for the particular value should be assumed.

As used herein and in the appended claims, the singular forms "a," "an," and "the," include plural referents unless the context clearly indicates otherwise. Thus, for example, reference to "a molecule" includes one or more of such molecules, "a resin" includes one or more of such different resins and reference to "the method" includes reference to equivalent steps and methods known to those of ordinary skill in the art that could be modified or substituted for the methods described herein.

While the above description provides examples and specific details of various embodiments, it will be appreciated that some features and/or functions of the described embodiments admit to modification without departing from the scope of the described embodiments. The above description is intended to be illustrative of the invention, the scope of which is limited only by the language of the claims appended hereto.

EXAMPLES

Aspects of the applicant's teachings may be further understood in light of the following examples, which should not be construed as limiting the scope of the applicant's teachings in any way.

Example 1—Study Design and Patients

Patients (aged 6-45 years) diagnosed with Type 1 diabetes within the past 100 days were parallel-screened for this study. Patients were eligible to participate in the study if they had at least one diabetes-related autoantibody (microassayed insulin antibodies [if duration of insulin therapy was less than 7 days]; glutamic acid decarboxylase-65 [GAD-65] antibodies; islet-cell antigen-512 [ICA-512] antibodies; or islet-cell autoantibodies) and had stimulated C-peptide concentrations of 0.2 nmol/L or higher measured during a mixed-meal tolerance test (MMTT) done at least 21 days after diagnosis of diabetes and within 37 days of randomization.

People whose blood samples screened positive for serum antibodies to hepatitis B surface antigen, hepatitis C, or HIV were excluded from participation. Samples were also tested for Epstein-Barr virus (EBV). Individuals who had evidence of active EBV infection at the time of screening were ineligible. Participants who showed evidence of active EBV infection after randomization did not receive additional study drug until resolution.

Patients were randomly assigned in a 2:1 ratio, stratified by participating site, to receive experimental treatment with abatacept or placebo using a double blind protocol. Table 1 provides the baseline demographic and laboratory characteristics of participants

TABLE 1

|  | Abatacept (n = 77) | Placebo (n = 35) |
|---|---|---|
| Age |  |  |
| Mean (years) | 13·9 (6·9) | 13·7 (5·3) |
| Median (years) | 12 (6-36) | 14 (7-34) |
| Men | 41 (53%) | 25 (71%) |
| Race* White | 71 (93%) | 32 (91%) |
| Ethnic origin Non-Hispanic | 67 (87%) | 31 (89%) |
| Number of diabetes-related autoantibodies† |  |  |
| 1 | 9 (12 | 4 (11%) |
| 2 | 26 (34%) | 9 (26%) |
| 3 | 26 (34%) | 15 (43%) |
| 4 | 16 (21%) | 7 (20%) |
| Number of days from diagnosis to first infusion‡ | 87·9 (14·1) | 83·2 (17·8) |
| Weight (kg) | 52·6 (21·9) | 53·0 (19·7) |
| Body-mass index (kg/m$^2$) | 21·0 (4·5) | 20·5 (3·9) |
| Mean AUC for C-peptide (nmol/L) | 0·743 (0·42) | 0·745 (0·31) |
| HbA1c at baseline* (%) | 6·31% (0·80) | 6·74% (0·94) |
| Total daily insulin dose at baseline* (U/kg) | 0·385 (0·24) | 0·339 (0·22) |
| Ketoacidosis at diagnosis | 25 (32%) | 8 (23%) |
| Diabetes-associated HLA alleles present* |  |  |
| DR3 and DR4 | 25 (34%) | 16 (49%) |
| DR3 only | 11 (15%) | 5 (15%) |
| DR4 only | 30 (41%) | 10 (30%) |
| Neither | 8 (11%) | 2 (6%) |

Data are n (%), mean (SD), or median (range).
AUC = area under the curve.
HbA1c = glycated haemoglobin A1c.
*Excludes participants with data missing for indicated variable (number missing: race, 1; HbA1c, 2; insulin use, 1; HLA allele status, 4).
†Islet-cell autoantibodies by immunofluorescence not tested on 16 patients (considered negative for count).
‡Range 51-108 for abatacept group and 38-107 for placebo.

Example 2—Procedures

Abatacept (Orencia, Bristol-Myers Squibb, Princeton, N.J., USA) was given on days 1, 14, and 28, and then every 28 days with the last dose on day 700 (total 27 doses) as a 30-min intravenous infusion at a dose of 10 mg/kg (maximum 1000 mg per dose) in a 100 mL 0.9% sodium chloride infusion. Normal saline infusion was used as placebo. Patients did not receive any premedication.

All patients received intensive diabetes management. The goal was to achieve intensive glycaemic control as recommended by the American Diabetes Association. (American Diabetes Association. Diabetes Care 2011; 33 (suppl 1): S11-61.) Patients used either multiple daily insulin injections or an insulin pump. Blood glucose monitoring was done by means of frequent daily blood glucose monitoring. Use of non-insulin pharmaceuticals that affect glycaemic control was not allowed.

Blood samples were analyzed centrally. C-peptide concentrations were measured from frozen plasma with a two-site immunoenzymometric assay (Tosoh Bioscience, South San Francisco, Calif., USA). Glycated haemoglobin A1c (HbA1c) was measured with ion-exchange high-performance liquid chromatography (Variant II, Bio-Rad Diagnostics, Hercules, Calif., USA). Reliability coefficients for each assay were greater than 0.99 from split duplicate samples. Biochemical autoantibodies (microassayed insulin antibodies, GAD-65 antibodies, ICA-512 antibodies) were measured with radioimmunobinding assays and islet-cell autoantibodies (ICA) with indirect immunofluorescence. A routine chemistry panel was done (Roche Diagnostics [Indianapolis, Ind., USA] Hitachi 917 Analyzer and reagents). HLA class II alleles were measured with PCR amplification and sequence-specific hybridization. β-cell function was assessed by stimulated C-peptide secretion. The prespecified primary outcome of this trial was a comparison of the area under the curve (AUC) of stimulated C-peptide response over the first 2 h of a 4-h MMTT2, done at the 24-month visit. The 4-h MMTTs were done at baseline and at 24 months; 2-h MMTTs were obtained at 3, 6, 12, and 18 months. Patients who had completed their 2-year visit MMTT were included in the primary outcome assessment. After completion of the 2-year treatment phase, participants entered a 2-year follow-up phase (study remained double blind) to continue to assess safety and efficacy, including an MMTT every 6 months. Prespecified secondary outcomes included: slope of C-peptide over time, difference between groups in incidence of loss of peak C-peptide to less than 0.2 nmol/L, differences in HbA1c and insulin dose over time, and safety. Prespecified subgroup factors included age, sex, race, baseline C-peptide, baseline insulin use, baseline HbA1c, and HLA type.

Example 3—Statistical Analyses

Spotfire S+8.1, a statistical analysis software, was used for all analyses. A sample size of 108 participants was planned to provide 85% power to detect a 50% increase in geometric mean C-peptide relative to the placebo group using a test at the 0.05 level (one-sided), with 10% loss to follow-up and a 2:1 allocation to treatment versus control (based on an estimated mean of 0.248 and SD of 0.179, on the transformed scale). All analyses were based on the prespecified intention to treat cohort with known measurements. Missing values were assumed to be missing at random. The p values associated with the intention-to-treat treatment comparisons of the primary and secondary endpoints are two-sided, although the design of the trial was based on a one-sided hypothesis test. Interim analysis for endpoint treatment effect was done and reported to the data and safety monitoring board once in accordance to the method of Lan and DeMets with O'Brien-Fleming boundaries. (Lan K K G, DeMets D L. *Biometrika* 1983; 70: 659-63.) The prespecified analysis method for C-peptide mean AUC, HbA1c, and total daily insulin dose was an analysis of covariance model adjusting for age, sex, and baseline value of the dependent variable, and treatment assignment. The predicted means and associated 95% confidence intervals (CIs) for each treatment group were established at the means of the other covariates. The significance levels associated with the treatment effect were from the Wald test (from the fitted model). A normalizing transformation of log(XC-Pep+1) was prespecified for C-peptide AUC mean, and normal plots of the residuals suggested that it was adequate. The C-peptide mean AUC equals the AUC divided by the 2-h interval (i.e., AUC/120). The AUC was computed using the trapezoidal rule from the timed measurements of C-peptide during the MMTT. The time to first stimulated peak C-peptide of less than 0.2 nmol/L (a level above which was associated with decreased risk of complications) was analyzed with standard survival methods (Cox model and Kaplan-Meier method). Adverse event grades were analyzed with the Wilcoxon rank sum test. (Agresti A. Categorical data analysis. New York, N.Y., USA: John Wiley and Sons, 1990.) Mean rate of change of C-peptide mean AUC from 6 to 24 months was estimated with a mixed-effects model with both random intercept and slope adjusting for age, sex, baseline C-peptide mean AUC, and treatment assignment. The initial fit included a fixed interaction effect of treatment and time, but was removed because of the absence of any statistical evidence of it being other than zero. To assess the treatment effect over the entire time period, we fitted a similar mixed model to the data with the differences that we defined time without structure and grouped by 6-month intervals.

Example 4—Results

Of the 112 patients enrolled in the study, 77 were randomly assigned to receive experimental treatment with abatacept and 35 were assigned to receive placebo. Table 1 summarizes the baseline characteristics of the two groups. The only noteworthy imbalances were the greater proportion of men in the placebo group than in the abatacept group and higher mean HbA1c in the placebo group. The number of infusions actually administered by treatment group were compared using a Wilcoxon rank sum test; no significant difference was detected (p=0.61). Overall, 2514 (83%) of 3024 potential infusions were given, and many that were not given were per protocol (e.g., patient developed EBV infection or became pregnant). 689 (93%) of 738 expected MMTTs were done. In the primary analysis at 2 years, participants assigned to abatacept had a geometric mean stimulated C-peptide 2-h AUC of 0.375 nmol/L (95% CI 0.290-0.465) versus 0.266 nmol/L (0.171-0.368) for those assigned to placebo. The adjusted population C-peptide mean 2-h AUC at 2 years was 0.378 nmol/L for the abatacept group and 0.238 nmol/L for the placebo group; thus, C-peptide AUC at 2 years was 59% (95% CI 6.1-112) higher with abatacept (p=0.0029). The result remained unchanged and significant (p=0.0028) when baseline HbA1c was added as a covariate. To address the difference in C-peptide concentrations from baseline to the 2-year assessments (primary endpoint), C-peptide results for 3, 6, 12, and 18 months were separately modeled.

Figure 1:
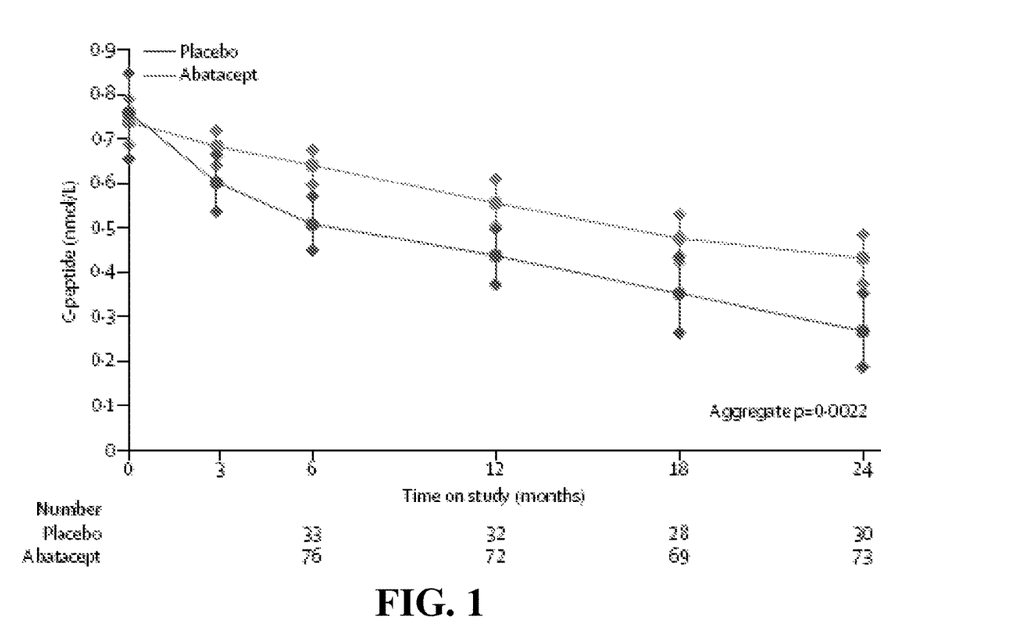
FIG. 1 is the population mean of stimulated C-peptide 2-h AUC mean over time for each treatment group. The estimates are from the ANCOVA model adjusting for age, sex, baseline value of C-peptide, and treatment assignment. Y-axis is on a log(y+1) scale. Error bars show 95% confidence intervals (CIs). AUC=area under the curve.
Figure 2:
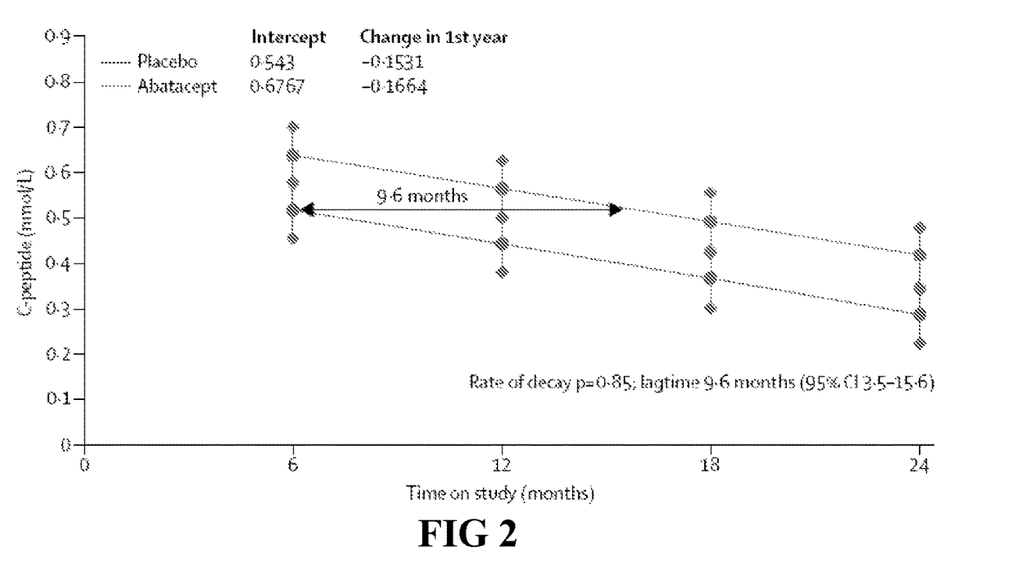
FIG. 2 is the predicted population mean of stimulated C-peptide 2-h AUC mean over time for each treatment group. Estimates are from the analysis of mixed-effects model adjusting for age, sex, baseline value of C-peptide, and treatment assignment, and including a fixed effect for time as a linear line on the log(y+1) scale. AUC=area under the curve.
Figure 3:
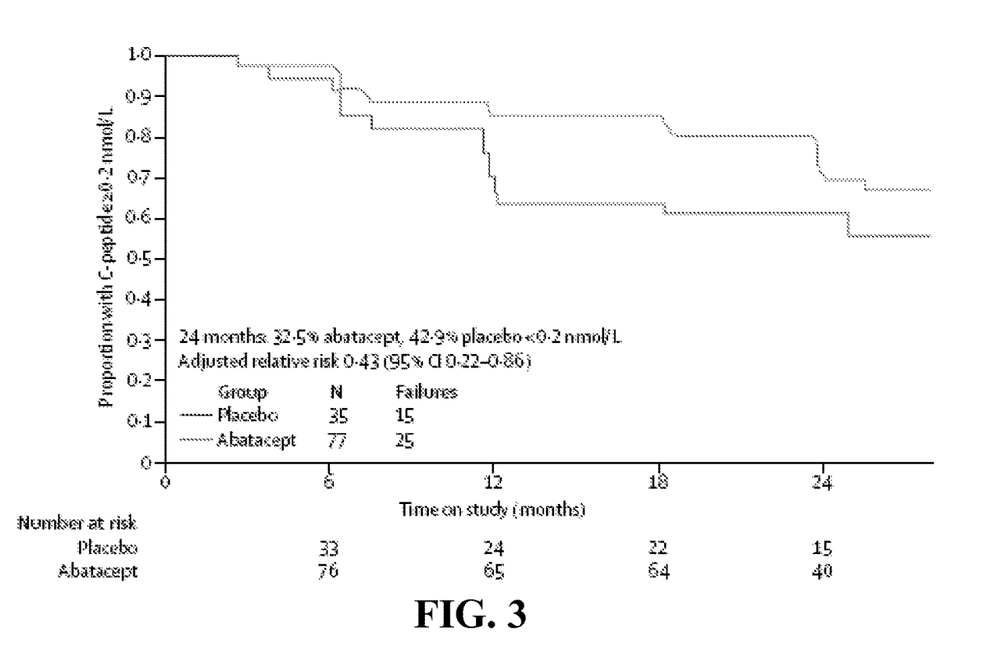
FIG. 3 is the proportion of participants with 2-h peak C-peptide remaining at or above 0.2 nmol/L over time for each treatment group.
Figure 4A:
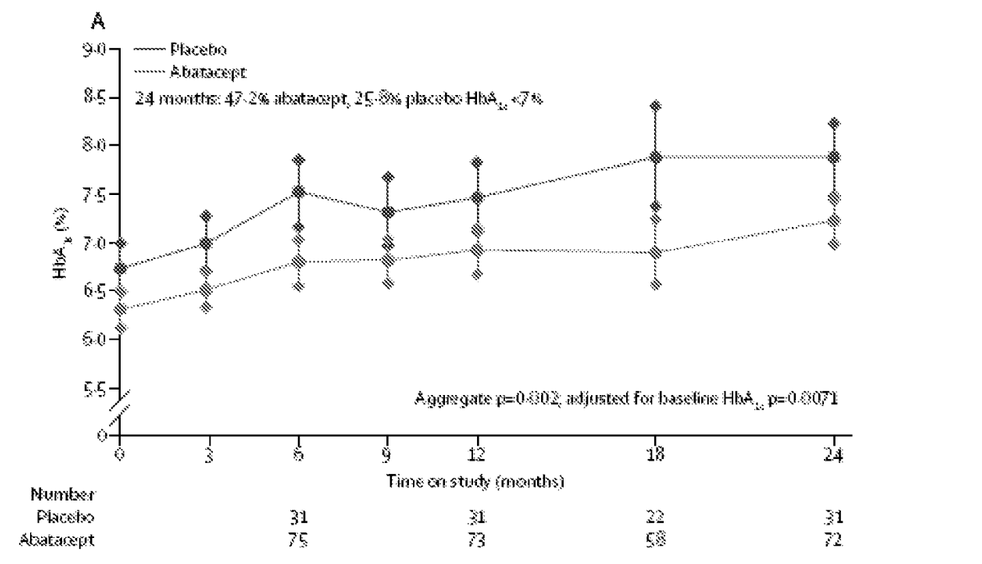
FIGS. 4A and 4B are the population mean of (A) HbA1c and (B) insulin use over time for each treatment group. Estimates are from the ANCOVA model adjusting for age, sex, baseline value of HbA1c, and treatment assignment. Insulin use is per kg of bodyweight, at 3-month intervals. Error bars show 95% CIs. HbA1c is glycated haemoglobin A1c.
Figure 4B:
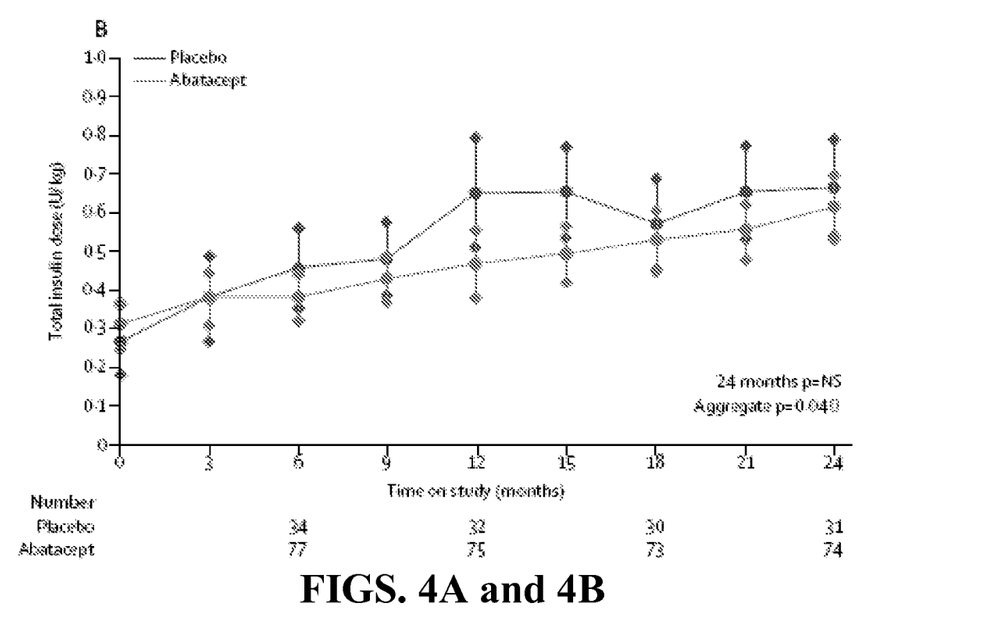

FIG. 1 shows the adjusted population C-peptide mean 2-h AUC over 2 years. Patients who received abatacept had a significantly higher mean AUC at 6, 12, and 18 months than did those assigned to placebo, and over all time points in aggregate (p=0.0022). To calculate the effect of treatment on delaying the reduction of C-peptide, we calculated the predicted population mean of C-peptide AUC mean by treatment group over time (FIG. 2). The lines are based on the fitting of a mixed linear model using all available data from MMTTs at 6, 12, 18, and 24 months. When testing for the improvement in the fit for the interaction term of slope and treatment (i.e., testing the evidence that the two treatment groups had differing C-peptide decay rates), this result was not significant (p=0.85). Consequently, a simpler model assuming identical slopes was used and FIG. 2 shows these results. Thus, estimated lag time in the means of the abatacept group to drop to the same level as those of the placebo group was 9.6 months (95% CI 3.47-15.6). By the 24-month assessment, (32%) patients in the abatacept group had an AUC peak stimulated C-peptide less than 0.2 nmol/L, compared with 15 (43%) patients on placebo (FIG. 3). The adjusted relative (abatacept to placebo groups) risk of peak C-peptide falling below 0.2 nmol/L was 0.433 (95% CI 0.218-0.861). During the 24 months of follow-up, the abatacept group had a lower adjusted mean HbA1c (FIG. 4A) than did the placebo group (for all time points in the aggregate, p=0.002), although HbA1c was also lower at baseline. Nonetheless, even after adjustment for the difference at baseline, the treatment group difference over 24 months persists (p=0.0071). At study end, 34 (47%) patients on abatacept had HbA1c lower than 7% compared with eight (26%) on placebo. This is particularly noteworthy as 86% of all patients were under 18 years of age; in this group this HbA1c is better that the ADA age-specific target HbA1c. Participants in the abatacept group had lower insulin doses at some time points (6 and 12 months) during the study, but at 24 months, insulin doses in the two groups were similar (FIG. 4; p=NS at 24 months, but because of differences at the earlier time points, p=0.040 for all time points in the aggregate).

Figure 5:
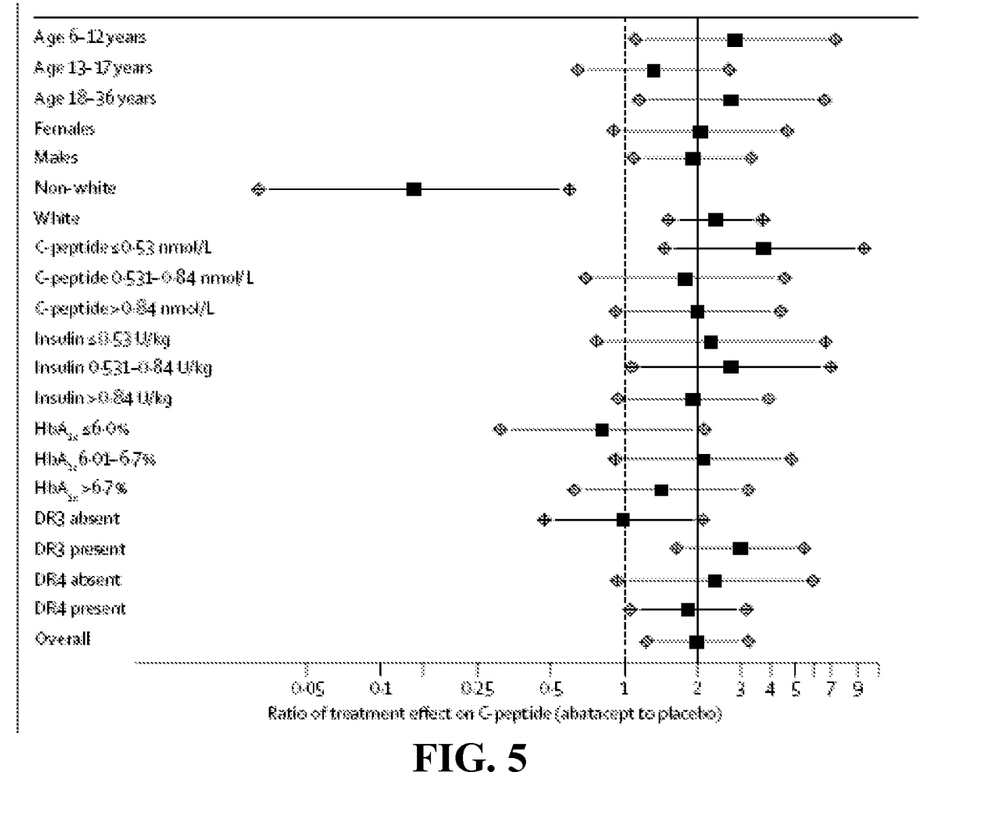
FIG. 5 is the ratio (abatacept to placebo) of treatment effect on 2-year stimulated C-peptide AUC mean within categories of prespecified baseline factors. Estimates are from the ANCOVA modeling log of C-peptide adjusting for age, sex, baseline value of C-peptide, the indicated categorized factor, treatment assignment, and treatment interaction terms. The homogeneity test of treatment effect was significant for DR3 allele status (p=0.025) and race (p=0.0003). AUC=area under the curve. HbA1c=glycated haemoglobin A1c.

FIG. 5 shows the results of a homogeneity test of treatment effect on age, sex, race, baseline C-peptide, baseline insulin use, baseline HbA1c, and HLA type. The apparent adverse effect of abatacept in non-white participants might be hypothesis-generating, however the groups size was small.

Table 2 and Table 3 summarize safety and adverse events. Abatacept was well tolerated. Infusion-related adverse events occurred with low frequency (47 of 2514 infusions [2%] involving 27 patients) and were not clinically significant. Of these, 36 reactions occurred in 17 (22%) of 77 patients on abatacept and 11 reactions in six (17%) of 35 patients on placebo (p=0.62 for proportion of participants by Fisher's exact test). Overall adverse event rate (including laboratory abnormalities) was low with no difference between the two groups. Specifically, there was no increase in infection (including EBV) or in neutropenia (which occurred in seven [9%] of patients on abatacept, five [14%] on placebo). There were seven episodes of hypoglycemia reported as an adverse event, two of which were severe hypoglycemia (one in each group).

TABLE 2

Number of patients by worst grade of adverse effects

|  | Abatacept (n = 77) | Placebo (n = 35) |
| --- | --- | --- |
| None | 14 (18%) | 8 (23%) |
| Grade 1 | 1 (1%) | 1 (3%) |
| Grade 2 | 44 (57%) | 17 (49%) |
| Grade 3 | 12 (16%) | 7 (20%) |
| Grade 4 | 5 (6%) | 2 (6%) |
| Grade 5 | 1 (1%)* | 0 |

Data are n (%). Worst grade by treatment group was not statistically different with a Wilcoxon Rank Sum Test.
*Accidental death, unrelated to study.

TABLE 3

Number of events and patients by type of adverse event

|  | Abatacept (n = 77) Number of events | Placebo (n = 35) Number of patients with events | Abatacept (n = 77) Number of events | Placebo (n = 35) Number of patients with events |
| --- | --- | --- | --- | --- |
| Allergy/immunology | 3 | 2 (3%) | 0 | 0 |
| Auditory/ear | 3 | 3 (4%) | 0 | 0 |
| Blood/bone marrow | 16 | 11 (14%) | 18 | 6 (17%) |
| Cardiac arrhythmia | 1 | 1 (1%) | 1 | 1 (3%) |
| Cardiac, general | 2 | 2 (3%) | 0 | 0 |
| Constitutional symptoms | 19 | 15 (19%) | 2 | 2 (6%) |
| Death* | 1 | 1 (1%) | 0 | 0 |
| Dermatology/skin | 15 | 13 (17%) | 5 | 4 (11%) |
| Endocrine | 4 | 4 (5%) | 2 | 2 (6%) |
| Gastrointestinal | 30 | 18 (23%) | 11 | 7 (20%) |
| Infection | 63 | 32 (42%) | 31 | 15 (43%) |
| Hypoglycaemia | 5 | 3 (4%) | 2 | 1 (3%) |
| Metabolic/laboratory† | 8 | 6 (8%) | 4 | 2 (6%) |
| Musculoskeletal/soft tissue | 13 | 11 (14%) | 7 | 6 (17%) |
| Neurology | 13 | 8 (10%) | 3 | 2 (6%) |
| Ocular/visual | 3 | 3 (4%) | 1 | 1 (3%) |
| Pain | 7 | 6 (8%) | 5 | 4 (11%) |
| Pulmonary/upper respiratory | 20 | 10 (13%) | 7 | 4 (11%) |
| Renal/genitourinary | 0 | 0 | 1 | 1 (3%) |
| Secondary malignancy | 1 | 1 (1%) | 0 | 0 |
| Sexual/reproductive function | 1 | 1 (1%) | 0 | 0 |
| Surgery/intraoperative injury | 2 | 2 (3%) | 0 | 0 |
| Syndromes | 9 | 9 (12%) | 5 | 5 (14%) |
| Total | 239 |  | 105 |  |

Data are n or n (%). Adverse effect category by treatment group was tested with a one-sided (alternative of higher frequency in abatacept group) Fisher's Exact Test; only constitutional symptoms were significant (p = 0 · 049).
*Accidental death, unrelated to study.
†Other than hypoglycaemia.

Example 5—Discussion

Results show that over 2 years co-stimulation modulation with abatacept slows the reduction in β-cell function in recent-onset Type 1 diabetes by 9.6 months. The early beneficial effect suggests that T-cell activation still occurs around the time of clinical diagnosis of Type 1 diabetes, even though the disease course has presumably been in progress for several years. However, despite continued administration of abatacept over 24 months, the fall in β-cell function in the abatacept group parallels that in the placebo group on the basis of the mixed-model results that included the time interval from 6 to 24 months. This subsequent reduction in β-cell function causes us to speculate that continuing T-cell activation subsides as the clinical course of the disease progresses. Nevertheless, the difference from the placebo group is maintained during drug administration. Further observation will establish whether the beneficial effect continues after cessation of monthly abatacept infusions. Follow up of these patient shows that the drug beneficial effect lasts beyond the drug administration for at least one year.

Abatacept was well tolerated, with no difference between the two groups in adverse events. However, a potential limitation to clinical applicability is that live vaccines cannot be used within 3 months of abatacept treatment. This factor might be important in view of the young age of the target population. The main effect seems to occur early after initiation of treatment with subsequent resumption of the fall in β-cell function. This pattern is reminiscent of the effects of anti-CD3, anti-CD20, and a GAD-65 vaccine, all of which showed some efficacy followed later by a reduction in β-cell function parallel to that in the control group. However this approach stands out as this has little or no appreciable side effects unlike the other interventions enlisted. This finding is consistent with our notion that there is an early window of opportunity after diagnosis in which T-cell activation is prominent. The 59% higher mean AUC C-peptide with abatacept than with placebo at 24 months in our study is similar to that seen with those other interventions, although direct comparison of studies is difficult because of differences in important baseline characteristics, including age, disease duration at time of randomization, and baseline HbA1c. Moreover, our study differs from those studies in that abatacept was administered continuously throughout the study, whereas in the case of anti-CD3, anti-CD20, and GAD-65 vaccine, administration of drug was completed within 2-4 weeks after randomization. Crucially, our study was not designed to establish whether a short treatment protocol would be sufficient to maintain improved C-peptide secretion over 2 years or whether a continuation of treatment is needed beyond 2 years. With all patients having completed their course of abatacept, the ongoing follow-up phase of the study will investigate whether the improved C-peptide secretion is sustained after discontinuation of the drug and for how long. Long-term follow-up of patients in one anti-CD3 trial showed diminishing difference in C-peptide secretion between the treated and the placebo group after 3 years. This is not the case for abatacept as the data one year off treatment shows that the beneficial effect is maintained, the difference in C-peptide preservation between the abatacept treated and the placebo group has not diminished (62% more C-peptide in the abatacept group at 3 years than the placebo group). In addition, the abatacept treated group HbA1c remained significantly better even after one year off treatment.

In the abatacept group, mean HbA1c was lower than that in the placebo group throughout the trial, although it was also lower at baseline. The maintenance of HbA1c lower than 7% for 18 months in the abatacept-treated group is noteworthy because 96 (86%) study participants were 18 years or younger. The clinical importance of HbA1c at this improved level has been well documented. (The Diabetes Control and Complications Trial Research Group. *N Engl J Med* 1993; 329: 977-86.) Insulin use was similar in the two groups and thus did not contribute to the difference in HbA1c. In our trial, abatacept-treated patients with recent-onset Type 1 diabetes had more endogenous insulin production, measured by C-peptide, during the 2 years of study drug administration. The duration of these effects after discontinuation of abatacept is being tested in ongoing follow-up of these patients. The one-year-off-therapy data shows that the beneficial effects of abatacept persist at least for one year beyond drug administration. The patients are being followed further. Abatacept administered over 2 years showed an excellent safety profile in patients with Type 1 diabetes. Its main effect seems to occur early after the initiation of treatment, however further studies are needed to test how far in the autoimmune process this drug can be effective in slowing down the autoimmunity. These approaches might be more easily tested with a subcutaneous version of abatacept.

The section headings used herein are for organizational purposes only and are not to be construed as limiting the subject matter described in any way.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A method of treating type 1 diabetes mellitus autoimmunity in a subject comprising administering an effective amount of a fusion protein composition which comprises a fusion protein and an oil-based carrier, wherein the fusion protein comprises the extracellular domain of CTLA4 and a portion of an immunoglobulin molecule and said oil-based carrier is an oil-in-water emulsion comprising Incomplete Freund's Adjuvant (IFA) or Montanide Incomplete Seppic Adjuvant (ISA).

2. The method of claim 1, wherein the oil-in-water emulsion comprises IFA.

3. The method of claim 1, wherein the oil-in-water emulsion comprises Montanide ISA.

4. A method of treating type 1 diabetes mellitus autoimmunity in a subject in need thereof, the method comprising administering a therapeutically effective regimen of a composition comprising a fusion protein to the subject,
    wherein the fusion protein comprises the extracellular domain of CTLA4 and a portion of an immunoglobulin molecule to the subject, and
    wherein the therapeutically effective regimen comprises administering an effective amount of the composition over a period of at least 6 months at a frequency between about once a day and about once every two months.

5. The method of claim 4, wherein the therapeutically effective regimen comprises administering the effective amount of the composition at a frequency of about once a week.

6. The method of claim 4, wherein the therapeutically effective regimen comprises administering the effective amount of the composition at a frequency of about once every two weeks.

7. The method of claim 4, wherein the therapeutically effective regimen comprises administering the effective amount of the composition at a frequency of about once a month.

8. The method of claim 4, wherein the therapeutically effective regimen comprises administering the effective amount of the composition at a frequency of about once every 2 months.

9. The method of claim 4, wherein the subject is human.

10. The method of claim 9, wherein at the time of beginning the administration of the therapeutically effective regimen the subject had been diagnosed with type 1 diabetes mellitus within the last 200 days.

11. The method of claim 10, wherein at the time of beginning the administration of the therapeutically effective regimen the subject had been diagnosed with type 1 diabetes mellitus within the last 100 days.

12. The method of claim 10, wherein at least once between the time of diagnosis and the time of beginning the administration of the therapeutically effective regimen, the subject had a stimulated C-peptide concentration of at least about 0.2 nmol/L as measured by a mixed-meal tolerance test (MMTT).

13. The method of claim 4, wherein at the time of beginning the administration of the therapeutically effective regimen the expression of at least one diabetes-related autoantibody had been detected in the subject.

14. The method of claim 4, wherein the subject receives daily insulin during the administration of the therapeutically effective regimen.

15. The method of claim 4, wherein the therapeutically effective regimen comprises administering the effective amount of the composition over a period of at least one year.

16. The method of claim 15, wherein the therapeutically effective regimen comprises administering the effective amount of the composition over a period of at least two years.

17. The method of claim 4, wherein the effective amount is between about 5 mg/kg and 50 mg/kg.

18. The method of claim 4, wherein the composition comprises an oil-based carrier which is an oil-in-water emulsion comprising Incomplete Freund's Adjuvant (IFA) or Montanide Incomplete Seppic Adjuvant (ISA).

19. The method of claim 4, further comprising measuring levels of C-peptide in the subject at least about once every six months during the administration of the therapeutically effective regimen.

20. A method of treating type 1 diabetes mellitus in a human subject diagnosed with type 1 diabetes mellitus within the last 100 days, the method comprising administering a therapeutically effective regimen of a composition comprising a fusion protein to the subject,
wherein the fusion protein comprises the extracellular domain of CTLA4 and a portion of an immunoglobulin molecule to the subject, and
wherein the therapeutically effective regimen comprises administering an effective amount of the composition over a period of at least 6 months at a frequency between about once a week and about once every two months.

* * * * *